United States Patent
Dahmen

(10) Patent No.: US 10,025,091 B2
(45) Date of Patent: Jul. 17, 2018

(54) OPTICAL INSTRUMENT HAVING SPRING-LOADED SEALING ELEMENT AT ONE OR BOTH SIDES OF AN END WINDOW

(71) Applicant: Karl Storz SE & Co. KG, Tuttlingen (DE)

(72) Inventor: Jan Dahmen, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 67 days.

(21) Appl. No.: 13/918,448

(22) Filed: Jun. 14, 2013

(65) Prior Publication Data

US 2013/0342906 A1    Dec. 26, 2013

(30) Foreign Application Priority Data

Jun. 14, 2012   (DE) .................. 10 2012 011 717

(51) Int. Cl.
   *G02B 27/00*   (2006.01)
   *A61B 1/00*    (2006.01)
   (Continued)

(52) U.S. Cl.
   CPC ........ *G02B 27/0006* (2013.01); *A61B 1/0011* (2013.01); *A61B 1/00096* (2013.01);
   (Continued)

(58) Field of Classification Search
   CPC .... G02B 21/0028; G02B 23/00; G02B 23/16; G02B 23/22; G02B 23/24; G02B 23/2476; G02B 23/2492; G02B 27/0006; A61B 1/00; A61B 1/00064; A61B 1/00071; A61B 1/0008; A61B 1/00066; A61B 1/0011;
   (Continued)

(56) References Cited

U.S. PATENT DOCUMENTS

| 3,071,129 A | 1/1963 | Wasserman |
| 5,311,858 A * | 5/1994 | Adair .......................... 600/106 |

(Continued)

FOREIGN PATENT DOCUMENTS

| DE | 19507205 A1 | 11/1995 |
| DE | 69923388 T2 | 12/2005 |

(Continued)

OTHER PUBLICATIONS

English Translation of Abstract of Muckner et al., DE 10 2008 031 881 B3, retrieved from EAST database dated Jan. 3, 2017.*

(Continued)

*Primary Examiner* — Stephone B Allen
*Assistant Examiner* — Ryan S Dunning
(74) *Attorney, Agent, or Firm* — Whitmyer IP Group LLC

(57) ABSTRACT

An optical instrument, in particular an endoscope, with a hollow instrument housing for receiving optical elements, wherein the distal end and/or proximal end is closed in a fluid-tight manner via an end window. In order to create an optical instrument which, while being easy to assemble, ensures a reliable fluid-tight seal of the instrument housing even during autoclaving, it is proposed according to the invention that the end windows are each sealed off in a fluid-tight manner with respect to the instrument housing via at least one spring-loaded sealing element.

17 Claims, 5 Drawing Sheets

(51) Int. Cl.
 *G02B 23/24* (2006.01)
 *G02B 7/02* (2006.01)
(52) U.S. Cl.
 CPC ...... *A61B 1/00137* (2013.01); *A61B 1/00195* (2013.01); *G02B 23/2476* (2013.01); *G02B 23/2492* (2013.01); *G02B 7/026* (2013.01); *G02B 23/2423* (2013.01); *G02B 23/2453* (2013.01)
(58) Field of Classification Search
 CPC ............ A61B 1/00131; A61B 1/00137; A61B 1/00096; A61B 1/00142; A61B 1/00163; A61B 1/015; A61B 1/127; A61B 1/253
 USPC ........ 359/507, 511, 513; 600/101, 133, 173, 600/127–130, 162, 169–171, 175, 176; D24/137, 138
 See application file for complete search history.

(56) References Cited

U.S. PATENT DOCUMENTS

| | | | |
|---|---|---|---|
| 5,459,609 A * | 10/1995 | Schrag | 359/513 |
| 6,547,721 B1 * | 4/2003 | Higuma et al. | 600/133 |
| 7,715,126 B2 | 5/2010 | Apel et al. | |
| 2005/0027168 A1 | 2/2005 | Strom et al. | |
| 2006/0250687 A1 * | 11/2006 | Karaki | G02B 21/0012 359/368 |
| 2006/0291068 A1 * | 12/2006 | Dahmen et al. | 359/643 |
| 2007/0179341 A1 * | 8/2007 | Okada | 600/156 |
| 2007/0280091 A1 * | 12/2007 | Apel | G02B 7/026 369/275.1 |
| 2008/0281158 A1 * | 11/2008 | Miyagi | A61B 1/00114 600/152 |
| 2013/0090529 A1 * | 4/2013 | Boulais | A61B 1/0052 600/149 |
| 2013/0194411 A1 * | 8/2013 | Baleine | G02B 7/028 348/82 |

FOREIGN PATENT DOCUMENTS

DE 102008031881 B3 * 6/2009 .......... A61B 1/0008
JP H07199090 A 8/1995

OTHER PUBLICATIONS

European Search Report Application No. 13002818.6 dated Jun. 1, 2017 8 pages.

* cited by examiner

OPTICAL INSTRUMENT HAVING SPRING-LOADED SEALING ELEMENT AT ONE OR BOTH SIDES OF AN END WINDOW

FIELD OF THE INVENTION

The invention relates to an optical instrument, in particular an endoscope, with a hollow instrument housing for receiving optical elements, wherein it is closed in a fluid-tight manner at the distal end and/or proximal end via an end window.

BACKGROUND OF THE INVENTION

Endoscopes and other optical medical instruments have to be sterilized before each use. This sterilization is nowadays carried out by autoclaving, in which the optical instruments undergo a treatment with hot steam at a pressure in excess of 3 bar and a temperature in excess of 130° C.

To ensure that no moisture gets into the instrument housing under high thermal loading, it is known in practice for the terminal end windows, used as cover glasses and/or end lenses, to be connected to the instrument housing in a fluid-tight manner by adhesive bonding, welding or soldering.

An optical instrument of the type in question is known from DE 195 07 205 C2, for example.

However, since the materials used have different coefficients of thermal expansion, considerable stresses always arise, which can lead to cracks and/or stress fractures and, consequently, to loss of sealing.

Moreover, an autoclavable endoscope is known from DE 699 23 388 T2. In order to protect the instrument housing against entry of moisture during autoclaving, a water-tight cap or a nonreturn valve cap is provided that can be secured on the housing of the lens system.

Although these additional cover caps ensure reliable sealing of the instrument housing, this known construction has the disadvantages that, on the one hand, a separate component part has to be made available and, on the other hand, the sealing of the instrument housing necessitates an additional assembly step, namely the attachment of the cover cap.

SUMMARY OF THE INVENTION

Proceeding from this, the object of the invention is to create an optical instrument which, while being easy to assemble, ensures a reliable fluid-tight seal of the instrument housing even during autoclaving.

According to the invention, this object is achieved by the fact that the optical components are each sealed off in a fluid-tight manner with respect to the instrument housing via at least one spring-loaded sealing element.

By the use of a spring-loaded sealing element according to the invention, i.e. the combination of a traditional sealing element, for example an O-ring, with a spring element acting on the sealing element, a defined contact pressure of the respective end window against the instrument housing is obtained which ensures the necessary fluid tightness.

The elasticity of the spring element and that of the sealing element compensate for the thermal stresses that occur during autoclaving, without the fluid tightness being lost.

According to a practical embodiment of the invention, it is proposed that the sealing elements are each spring-loaded in the direction of the respective end window via at least one spring element. In addition to compensating for the thermal stresses, the spring elements serve to ensure that the sealing elements are pressed against the respective end windows with a contact pressure that remains constant over the lifetime of the sealing elements. Since the material properties of plastics on sealing elements can change over the lifetime of the sealing elements and have a greater or lesser tendency to flow, the contact pressure of the sealing elements against the end windows could decrease over time, unless a defined contact pressure were to be exerted on the sealing element by the spring elements according to the invention.

In a first embodiment of the invention, it is proposed that the spring elements bear directly on the associated sealing element.

Alternatively, in a second embodiment of the invention, it is proposed that the spring elements each act on the associated sealing element via at least one pressure element, wherein the at least one pressure element is designed as a pressure sleeve, for example.

For the design of the spring elements, the invention proposes that the spring elements are designed as spring disks or spring sleeves, wherein the spring disks are preferably mounted at one end in a radially surrounding groove, for example in the instrument housing.

In order to strengthen the sealing force on each end window that is to be sealed off in a fluid-tight manner, the invention further proposes that at least one sealing element is arranged upstream and downstream of each end window in the axial direction of the instrument housing, wherein, according to a practical embodiment of the invention, the sealing elements on both sides are each spring-loaded in the direction of the respective end window via at least one spring element.

Finally, the invention proposes that the end windows are designed as a cover glass and/or end lens.

BRIEF DESCRIPTION OF THE DRAWINGS

Further features and advantages of the invention will become clear from the attached drawings in which five illustrative embodiments of an optical instrument according to the invention are depicted purely by way of example, without limiting the invention to these illustrative embodiments. In the drawings.

DETAILED DESCRIPTION OF THE INVENTION

Figure 1:
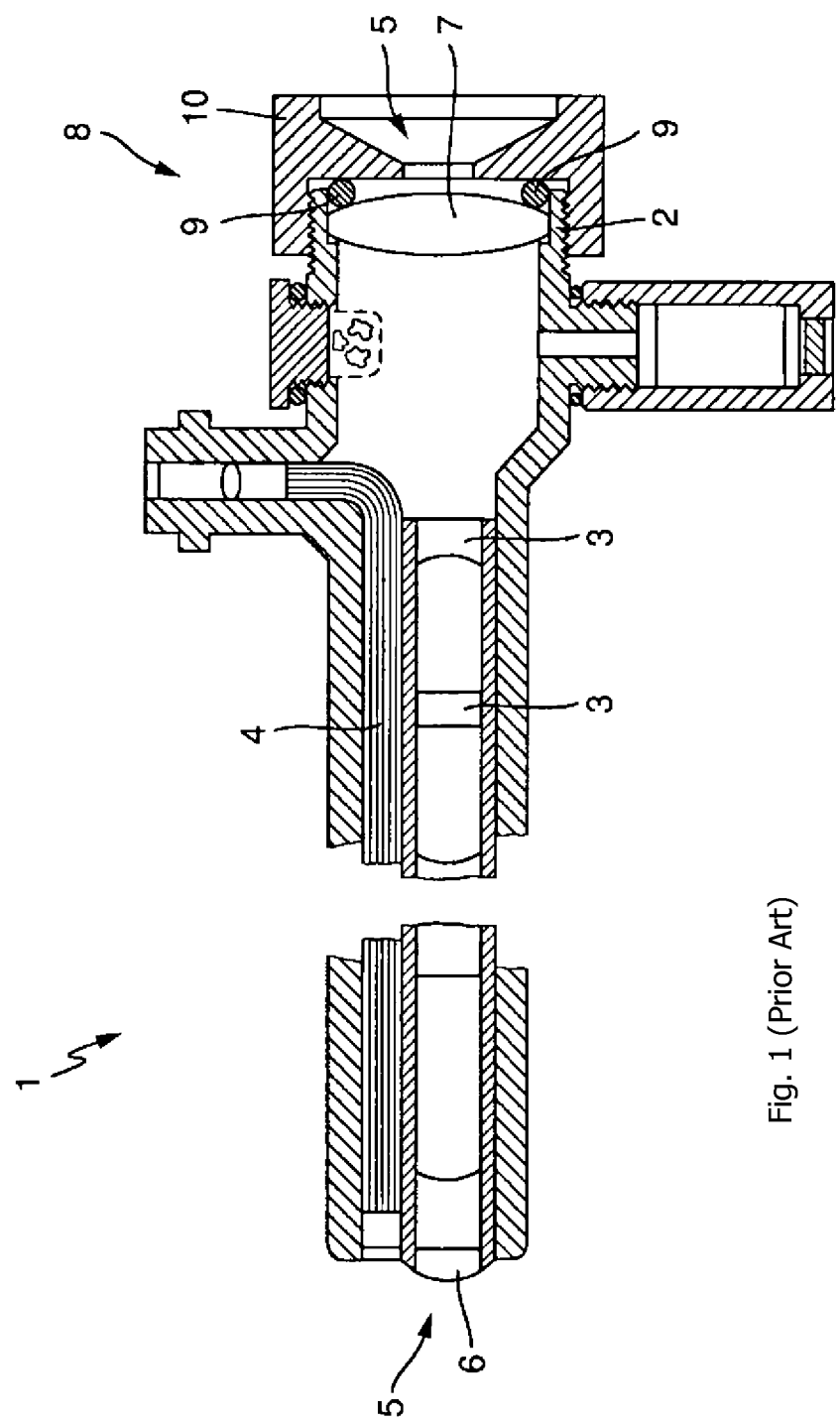
FIG. 1 shows a schematic longitudinal section through an optical instrument designed as an endoscope in accordance with the prior art.

The view in FIG. 1 is a schematic representation of the structure of an optical instrument 1 designed as an endoscope in accordance with the prior art. The optical instrument 1 has a hollow instrument housing 2 in which various optical elements, for example a plurality of lenses 3 and a bundle of light-carrying fibers 4, are arranged.

At the distal end and the proximal end, the instrument housing 2 is closed in a fluid-tight manner via a respective end window 5. In the optical instrument 1 depicted in FIG. 1, the end window 5 at the distal end is designed as an end lens 6, and the end window 5 at the proximal end is designed as a cover glass 7 of an eyepiece unit 8. In the optical instruments 1 known from the prior art, the fluid tightness at the ends of the instrument housing 2 is achieved by the fact that the end windows 5 are secured in the instrument housing 2 by adhesive bonding or soldering, or by the use of sealing elements 9.

During the autoclaving of the optical instruments 1, considerable stresses occur on account of the different coefficients of thermal expansion of the materials used, particularly in the case of end windows 5 that are adhesively bonded or welded rigidly to the instrument housing 2, and these stresses can lead to cracks and/or stress fractures and, consequently, to loss of sealing. However, under the conditions used in autoclaving, elastic sealing elements 9, for example O-rings 9, also age in such a way that the elasticity of the sealing elements 9 decreases over the course of time, which can in turn lead to loss of sealing.

In the optical instruments 1 depicted in the views in FIG. 2 to FIG. 7, the fluid tightness between the proximal and/or distal end windows 5 and the instrument housing 2 is obtained via spring-loaded sealing elements 9, which are preferably designed as O-rings 9.

Figure 2:
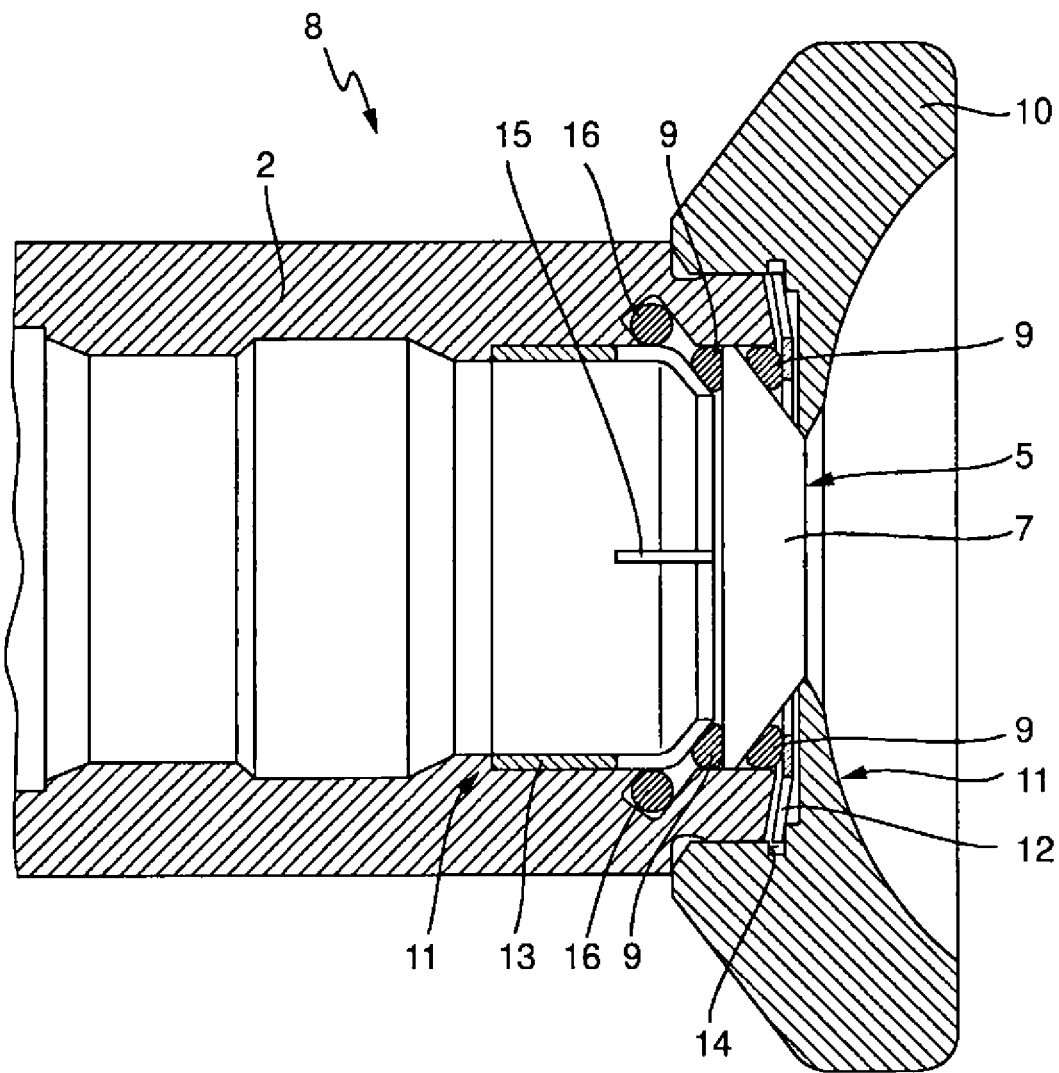
FIG. 2 shows a schematic section through the proximal end of an optical instrument according to the invention, representing a first embodiment according to the invention.

FIG. 2 shows schematically the structure of an eyepiece unit 8 of an optical instrument 1, for example of an endoscope for medical or non-medical purposes.

The eyepiece 8 depicted is composed principally of an eyepiece cup 10, arranged on the proximal end of the instrument housing 2, and of the end window 5, which is designed as a cover glass 7 and closes the instrument housing 2 in a fluid-tight manner at the proximal end.

In the eyepiece unit 8 depicted, the fluid tightness between the cover glass 7 and the instrument housing 2 is provided by spring-loaded sealing elements 9 designed as O-rings 9. In the first embodiment, depicted in FIG. 2, sealing elements 9 designed as O-rings 9 are arranged upstream and downstream of the cover glass 7 in the axial direction of the instrument housing 2, which sealing elements 9 are each spring-loaded in the direction of the cover glass 7 via a spring element 11.

By means of the spring elements 11, the sealing elements 9 are always pressed against the cover glass 7 with a sufficient sealing pressure to ensure that a fluid-tight seal is guaranteed even when thermally induced changes in length occur. Furthermore, by means of their being pretensioned, the spring elements 11 compensate for possible loss of elasticity of the sealing elements 9, which loss can occur in the sealing elements over the course of time as a result of material stress.

According to the embodiment depicted in FIG. 2, the spring elements 11 that pretension the sealing elements 9 in the sealing direction are designed as a spring disk 12, mounted at the proximal end in the eyepiece cup 10, and a spring sleeve 13, mounted distally and coaxially on the instrument housing 2.

The spring disk 12 is received and mounted in the eyepiece cup 10 in a radially surrounding groove 14, in which the spring disk 12 is mounted at one end. With the radially inner edge, the spring disk 12 bears on the sealing element 9 designed as O-ring 9, such that the latter is pretensioned in the direction of the cover glass 7.

The spring sleeve 13, which exerts a spring force on the distal sealing element 9, is bent radially inward at its proximal end and is provided with slits 15 extending in the axial direction in order thereby to be able to exert a radially outward spring force that acts on the associated sealing element 9.

As will also be seen from FIG. 2, a hygroscopic substance acting as desiccant 16 is arranged in the instrument housing 2 so that any moisture developing in the housing interior is bound to the desiccant before it is able to settle on the lenses 3. Even when the optical instrument is made fluid-tight in relation to the environment by means of the spring-loaded sealing elements 9, it is possible, for example already during the production of the optical instrument 1 in a normal atmosphere, for residual moisture of the atmospheric air to settle in the housing interior, which could later lead to clouding of the lenses 3.

The arrangement of the desiccant 16 is depicted purely by way of example in FIG. 2. The desiccant 16 can also be arranged at another place in the instrument housing 2 and can also have any other desired shape. It will further be noted that, for better clarity, desiccant 16 has been indicated only in FIG. 2, although it can also be arranged in the interior of the instrument housing 2 in each of the embodiments depicted in FIG. 3 to FIG. 7.

Figure 3:
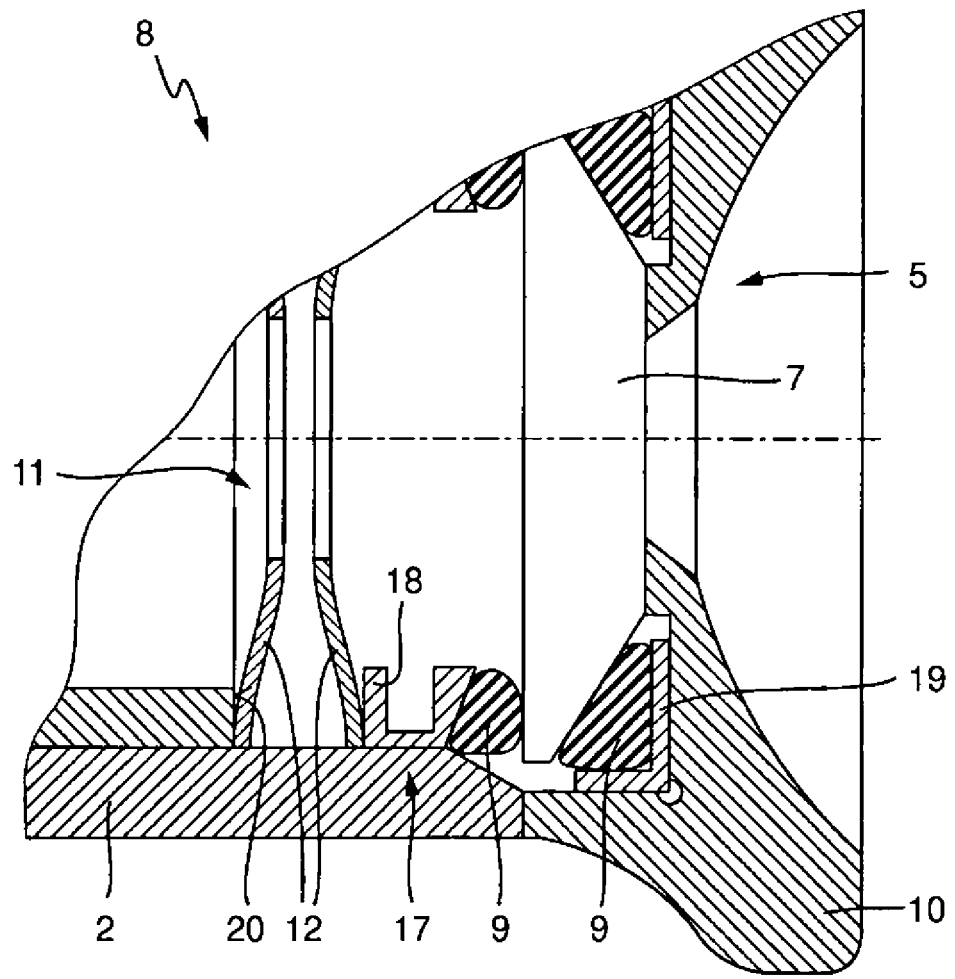
FIG. 3 shows a view according to FIG. 2, but representing a second embodiment according to the invention.

FIG. 3 shows a second embodiment for forming a fluid-tight seal between an end window 5 and the instrument housing 2, likewise taking the example of an eyepiece unit 8.

As will be seen from FIG. 3, sealing elements 9 designed as O-rings 9 are arranged upstream and downstream of the eyeglass 7 in this embodiment too, as viewed in the axial direction of the instrument housing 2.

In contrast to the embodiment according to FIG. 2, in which the spring elements 11 that pretension the sealing elements 9 in the sealing direction bear directly on the respective sealing elements 9, in the second embodiment the spring force is not transmitted directly to the sealing elements 9, but instead via at least one interposed pressure element 17, for example a pressure sleeve 18.

The structure of the fluid-tight seal in this embodiment is such that the proximal sealing element 9 is arranged in a radially inwardly facing angle piece 19 of the instrument housing 2 and is held in this position by the cover glass 7 adjoining it distally in the axial direction.

To generate the required sealing force, a spring element 11 composed of two spring disks 12 is arranged further distally in the axial direction. The two spring disks 12 are designed such that their radially outer edges are spaced apart from each other in the axial direction and are able to be pressed together toward each other by spring elasticity. Since one spring disk 12 is supported on an abutment 20 of the instrument housing 2 and the other spring disk 12 bears on an axially displaceable pressure sleeve 18, the proximally directed spring force of the spring element 11 is applied to the two sealing elements 9 via the pressure sleeve 18. The spring force is transmitted by the pressure sleeve 18 directly to the distal sealing element 9, which is pressed sealingly against the cover glass 7 via the pressure sleeve 18. By means of this pressure force applied in the proximal direction to the cover glass 7, the proximal sealing element 9 is pressed sealingly into the angle piece 19 of the instrument housing 2 via the cover glass 7.

By virtue of the structure indicated here, both sealing elements 9 are subjected to a spring force by the one spring element 11 such that the cover glass 7 closes the instrument housing 2 in a fluid-tight manner at the proximal end.

Figure 4:
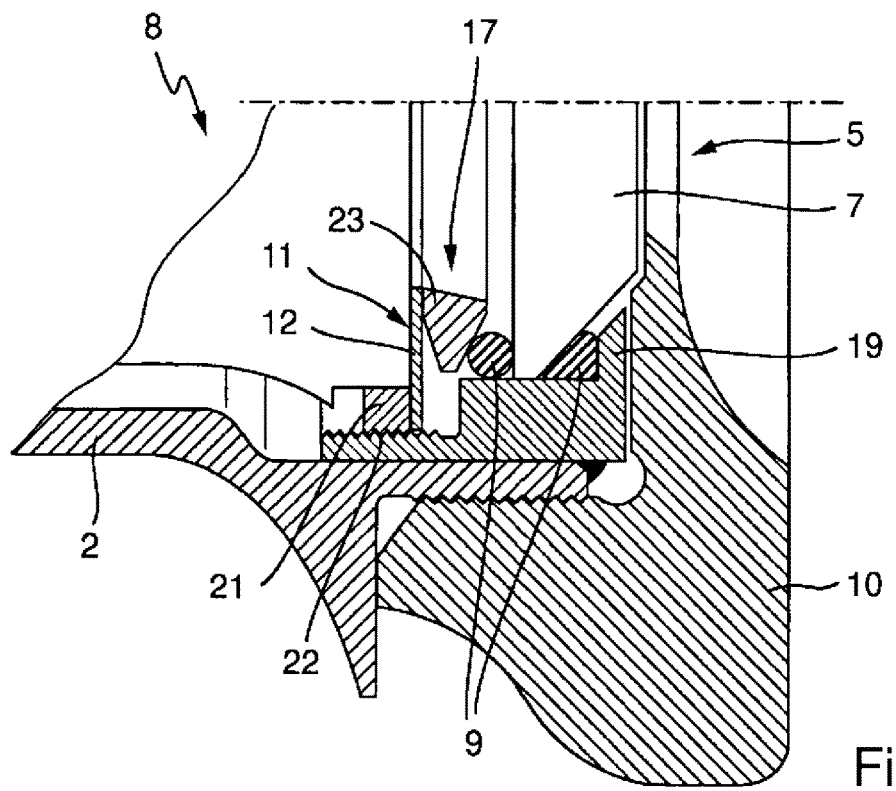
FIG. 4 shows a view according to FIG. 2, but representing a third embodiment according to the invention.

The third embodiment, depicted in FIG. 4, for forming a fluid-tight seal between an end window 5 and the instrument housing 2 again shows an eyepiece unit 8.

This design differs from the embodiment described above with reference to FIG. 3 in that the spring element 11 is composed of only one spring disk 12, which is mounted with its radially outer edge on a screw ring 21, which for its part is movable in the axial direction of the instrument housing 2 via a threaded path 22.

With its part protruding radially inward from the screw ring 21, the spring disk 12 bears on a pressure piece 23, which in turn bears on the distal sealing element 9.

By moving the screw ring 21 in the proximal direction, the spring disk 12 supported on the screw ring 21 is subjected to a proximally directed spring force, which acts on the two sealing elements 9 via the pressure piece 23. The spring force is transmitted directly by the pressure piece 23 to the distal sealing element 9, which is pressed sealingly against the cover glass 7 by the pressure piece 23. By means of this pressure force applied in the proximal direction to the cover glass 7, the proximal sealing element 9 is pressed sealingly into the angle piece 19 of the instrument housing 2 by the cover glass 7.

By virtue of the structure indicated here, both sealing elements 9 are subjected to a spring force by the spring disk 12 such that the cover glass 7 closes the instrument housing 2 in a fluid-tight manner at the proximal end. In this embodiment, the sealing force acting on the sealing elements 9 by way of the spring disk 12 can be adjusted via the screw ring 21 and, if appropriate, readjusted.

Figure 5:
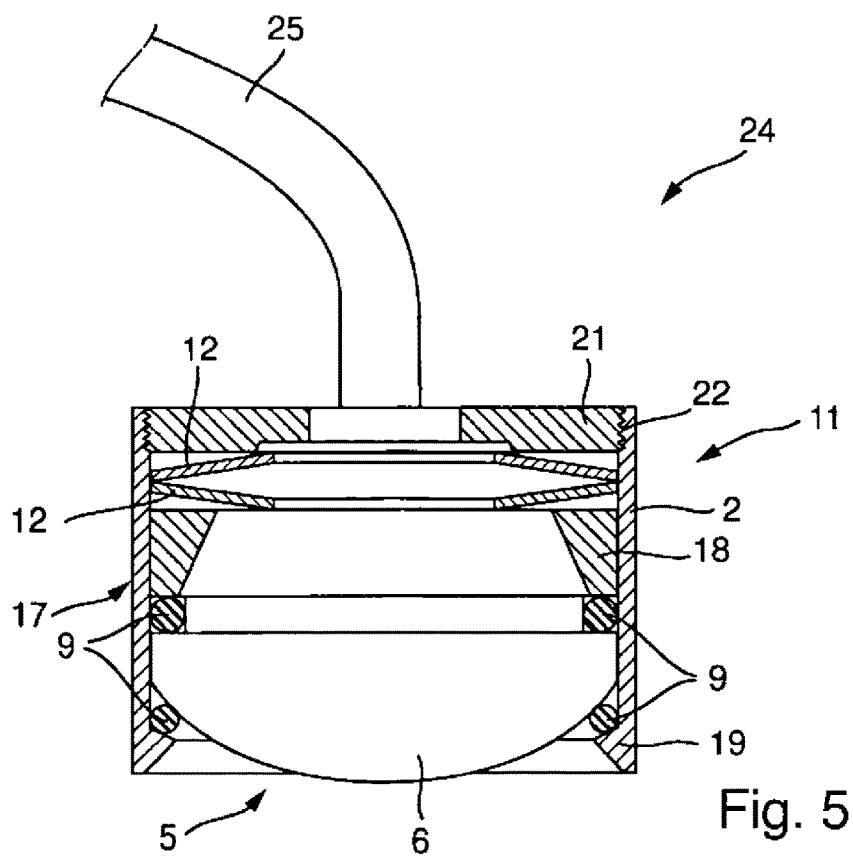
FIG. 5 shows a schematic section through the distal end of an optical instrument according to the invention, representing a fourth embodiment of the invention.

The fourth embodiment, depicted in FIG. 5, for forming a fluid-tight seal between an end window 5 and the instrument housing 2 shows the seal between a distally positioned end lens 6 and the instrument housing 2, taking the example of an optical instrument 1 designed as a lighting unit 24.

At the proximal end, this lighting unit 24 does not have an end window 5, and instead it has a connection for a light-carrying cable 25 via which light, coming from a light source (not shown), is transmitted to the lighting unit 24.

In the lighting unit 24 depicted, the fluid tightness between the end lens 6 and the instrument housing 2 is provided by spring-loaded sealing elements 9 designed as O-rings 9. In the embodiment depicted in FIG. 5, sealing elements 9 designed as O-rings 9 are arranged upstream and downstream of the end lens 6 in the axial direction of the instrument housing 2.

The structure of the fluid-tight seal in this embodiment is such that the distal sealing element 9 is arranged in a radially inwardly facing angle piece 19 of the instrument housing 2 and is held in this position by the end lens 6 adjoining it proximally in the axial direction. The end lens 6 is adjoined in the proximal direction by the second sealing element 9.

The angle piece 19, which protrudes partially beyond the end lens 6 in the distal direction, serves not only to form a bearing surface for the distal sealing element 9 but also to act as a scratch guard for the end lens 6.

In the embodiment according to FIG. 5, the sealing force required for the fluid-tight seal is generated via a spring assembly which is arranged in the proximal direction from the end lens 6 and is composed of two spring disks 12, and of which the spring force is not transmitted directly to the sealing elements 9, but instead via an interposed pressure sleeve 18.

The two spring disks 12 are designed such that their radially outer edges are bent toward each other, such that the spring disks 12 bear on each other only with their radially outer edges and are spaced apart from each other with spring elasticity in the central area.

By virtue of the fact that the proximal spring disk of the two spring disks 12 is mounted as an abutment on a screw ring 21, which for its part is movable in the axial direction of the instrument housing 2 via a thread path 22, and the other spring disk 12 bears on an axially displaceable pressure sleeve 18, the proximally directed spring force of the spring assembly is applied to the two spring elements 9 via the pressure sleeve 18. The spring force is transmitted directly by the pressure sleeve 18 to the proximal sealing element 9, which is pressed sealingly against the end lens 6 by the pressure sleeve 18. By means of this pressure force applied in the distal direction to the end lens 6, the distal sealing element 9 is pressed sealingly into the angle piece 19 of the instrument housing 2 by the end lens 6.

By moving the screw ring 21 in the distal direction, the two spring disks 12 are pressed together, as a result of which a distally directed spring force is generated that acts on the two sealing elements 9 via the pressure sleeve 18.

By virtue of the structure indicated here, both sealing elements 9 are subjected to a spring force by the two spring disks 12 such that the end lens 6 closes the instrument housing 2 in a fluid-tight manner at the proximal end. In this embodiment, the sealing force acting on the sealing elements 9 via the spring disks 12 can be adjusted via the screw ring 21 and, if appropriate, readjusted.

Figure 6:
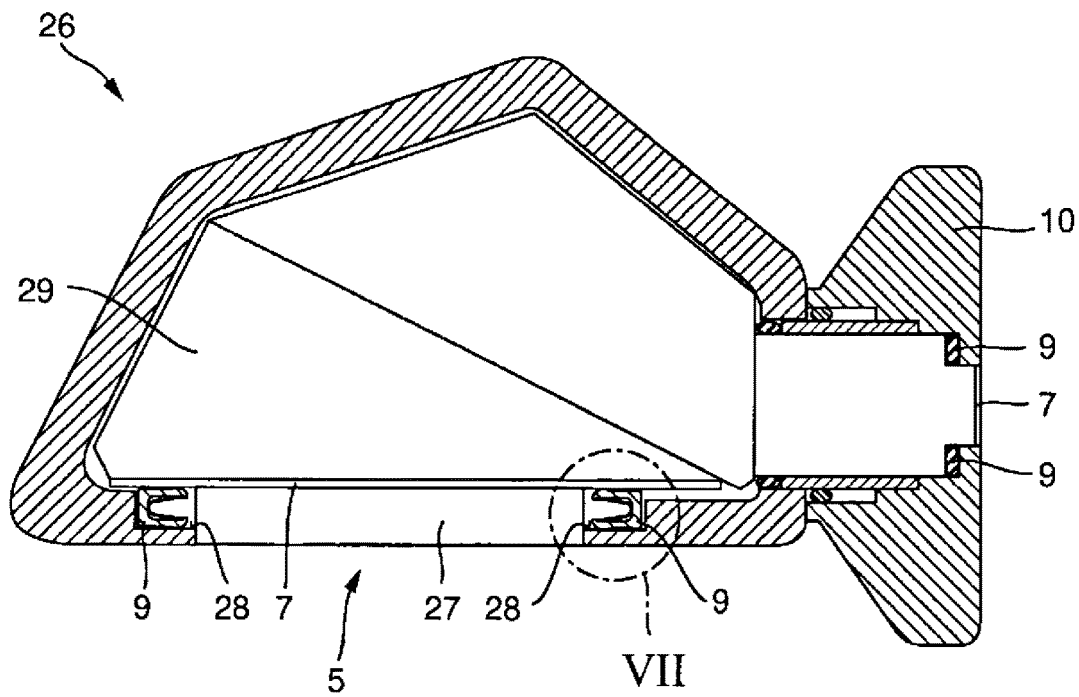
FIG. 6 shows a view according to FIG. 2, but representing a fifth embodiment according to the invention.
Figure 7:
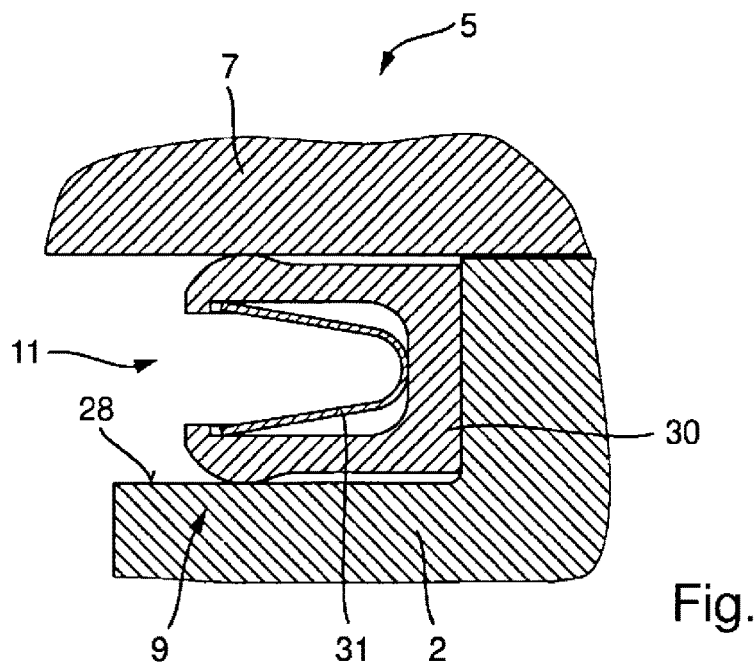
FIG. 7 shows an enlarged view of the detail VII according to FIG. 6.

The fifth embodiment, depicted in FIGS. 6 and 7, for forming a fluid-tight seal between an end window 5 and the instrument housing 2 shows the seal between a distally positioned cover glass 7 and the instrument housing 2, taking the example of an optical instrument 1 designed as an overview lens system 26.

At the proximal end, the overview lens system 26 has an eyepiece cup 10, of which the end window 5 designed as a cover glass 7 is sealed off with respect to the instrument housing 2 by sealing elements 9 (not shown) preferably designed as O-rings 9, for example as has been described above on the basis of the illustrative embodiments depicted in FIGS. 2, 3 and 4.

In the overview lens system 26 depicted, the fluid tightness between the cover glass 7 and the instrument housing 2 is provided by spring-loaded sealing elements 9, of which the precise structure can be seen from the enlarged view in FIG. 7. In the embodiment depicted in FIGS. 6 and 7, a spring-loaded sealing element 9 is arranged only distally in front of the cover glass 7.

The structure of the fluid-tight seal in this embodiment is such that the distal spring-loaded sealing element 9 is arranged on a shoulder 28 in the instrument housing 2, which shoulder 28 encloses a distal opening 27 of the instrument housing 2 and is designed as a return, and the spring-loaded sealing element 9 is held in this position on the shoulder 28 by the cover glass 7 adjoining it proximally. The cover glass 7 is adjoined in the proximal direction by a prism 29 secured in the instrument housing 2, wherein the cover glass 7 and the prism 29 bear directly on each other. If necessary, the contact face between the cover glass 7 and the prism 29 can also be coated with an optical gel.

In this embodiment, as can be seen in particular from FIG. 7, the sealing force required for the fluid-tight seal is generated by the fact that the spring-loaded sealing element 9 arranged on the shoulder 28 is designed as seal 30 of U-shaped cross section, wherein a spring element 11 designed as a V-shaped spring 31, and produced from spring steel for example, is arranged between the parallel legs of the U-shaped seal 30, and the spring force of the spring element 11 acts directly on the sealing element 9.

The use of this U-shaped seal 30 with the V-shaped spring 31 for forming the spring-loaded sealing element 9 has the advantage that the seal 30 with the V-shaped spring 31 secured therein can be prefabricated as a structural unit before this structural unit is inserted into the instrument housing 2. The U-shaped seal 30 is preferably made of a rubber-like material, although it is also possible to use soft plastics materials to form this seal 30.

The V-shaped spring 31 is designed, and arranged in the U-shaped seal 30, such that the two legs thereof bearing on the sealing element 9 apply a radially outwardly and obliquely downwardly directed force component to the sealing element 9. By means of this pressure force applied directly to the sealing element 9, the sealing element 9 is pressed sealingly against the cover glass 7. Since the proximal face of the cover glass 7 bears permanently as an abutment on the prism 29, it is sufficient in this embodiment to arrange a spring-loaded sealing element 9 only in the distal direction from the cover glass 7.

As an alternative to the embodiment depicted in FIGS. 6 and 7, in which the instrument housing 2 is closed at the distal end by a cover glass 7, it is however also possible to omit this cover glass 7, such that the instrument housing 2 is closed at the distal end directly by the prism 29. In this embodiment, the spring-loaded sealing element 9 arranged on the shoulder 28 of the instrument housing 2, and designed as a U-shaped seal 30 with an inner V-shaped spring 31, bears directly on the prism 29 and seals off the instrument housing 2 in a fluid-tight manner.

Although the spring elements 11 in FIG. 2 to FIG. 7 have mainly been depicted and described as spring disks 12 and spring sleeves 13, other designs of the spring elements 11 are of course also possible and can be used if they provide the above-described effect, namely that of generating a sufficient pressure force on the sealing elements 9.

All of the optical instruments 1 described above are distinguished by the fact that the proximal and/or distal end windows 5 are each sealed off in a fluid-tight manner with respect to the instrument housing 2 by at least one spring-loaded sealing element 9.

The elasticity of the spring element 11 and that of the sealing element 9 compensate for the thermal stresses that occur during autoclaving, without leaks occurring.

In addition to compensating for the thermal stresses, the spring elements 11 serve to ensure that the sealing elements 9 are pressed against the respective end windows 5 with a pressure that remains constant over the lifetime of the sealing elements 9.

The invention claimed is:

1. An optical instrument, in particular an endoscope, with a hollow instrument housing for receiving optical elements, wherein a distal end and/or proximal end of the hollow instrument housing is closed in a fluid-tight manner via an end window,
wherein each end window is sealed off in a fluid-tight manner with respect to the instrument housing via at least one sealing element wherein the at least one sealing element is spring-loaded via at least one spring element in a direction of the respective end window in such a way, that the respective end window is pressed in a sealing manner against the instrument housing, and wherein the at least one spring element is configured as an independent structural part which is fixable inside the optical instrument; and
wherein at least one spring-loaded sealing element is arranged upstream and downstream of each end window in an axial direction of the instrument housing.

2. The optical instrument of claim 1, wherein each spring-loaded sealing element is spring-loaded in the direction of the respective end window via the at least one spring element.

3. The optical instrument of claim 2, wherein each spring element bears directly on the associated sealing element.

4. The optical instrument of claim 2, wherein each spring element acts on the associated sealing element via at least one pressure element.

5. The optical instrument of claim 1, wherein each spring-loaded sealing element is designed as an O-ring.

6. The optical instrument of claim 2, wherein each spring element is designed as a spring disk or a spring sleeve.

7. The optical instrument of claim 6, wherein each spring element is designed as a spring disk, and the spring disks are mounted at one end in a radially surrounding groove.

8. The optical instrument of claim 4, wherein each pressure element is designed as a pressure sleeve.

9. The optical instrument of claim 1, wherein the spring-loaded sealing elements on both sides of each end window are each spring-loaded in the direction of the respective end window via the at least one spring element.

10. The optical instrument of claim 2, wherein the at least one spring-loaded sealing element is designed as a U-shaped seal arranged on a shoulder of the instrument housing, wherein the at least one spring element is designed as a V-shaped spring, which is arranged between the legs of the U-shaped seal.

11. The optical instrument of claim 1, wherein each end window is designed as a cover glass and/or end lens.

12. An optical instrument, in particular an endoscope, with a hollow instrument housing for receiving optical elements, wherein an end of the hollow instrument housing is closed in a fluid-tight manner via an end window,
wherein the end window is pressed in a sealing manner against the instrument housing via at least one sealing element wherein the at least one sealing element is spring-loaded and bears directly on the end window via a spring element in a direction of the respective end window, and wherein the spring element is configured as an independent structural part which is fixable inside the optical instrument; and
wherein each spring element bears directly on the associated sealing element.

13. The optical instrument of claim 12, wherein each spring element acts on the associated sealing element via at least one pressure element.

14. An optical instrument, in particular an endoscope, with a hollow instrument housing for receiving optical elements, wherein an end of the hollow instrument housing is closed in a fluid-tight manner via an end window;
wherein the end window includes a first side and a second side, with at least one sealing element bearing directly on each of the first side and the second side of the end window;
wherein the at least one sealing element on the first side of the end window is spring-loaded via a spring element in a direction of the respective end window in such a way, that the respective end window is pressed in a sealing manner against the instrument housing, and wherein the spring element is configured as an independent structural part which is fixable inside the optical instrument; and wherein each spring element bears directly on the associated sealing element.

15. The optical instrument of claim 14, wherein the at least one sealing element on the second side of the end window is spring-loaded via the spring element in the direction of the respective end window.

16. The optical instrument of claim 14, wherein each spring element is designed as a spring disk or a spring sleeve.

17. The optical instrument of claim 14, wherein each spring element is a cylindrical coil.

* * * * *